United States Patent [19]

Nordström

[11] Patent Number: 5,803,731
[45] Date of Patent: Sep. 8, 1998

[54] METHOD FOR THE PRODUCTION OF A SUCTION HOSE FOR SALIVA EJECTION AND A SUCTION HOSE FOR SALIVA EJECTION

[75] Inventor: Kaj Arne Lennart Nordström, Vellingevägen, Sweden

[73] Assignee: Kanor Plast AB, Vellinge, Sweden

[21] Appl. No.: 755,389

[22] Filed: Nov. 22, 1996

[30] Foreign Application Priority Data

Nov. 23, 1995 [SE] Sweden .................................. 9504184

[51] Int. Cl.⁶ ...................................................... A61C 17/04
[52] U.S. Cl. ............................... 433/96; 433/94; 604/281
[58] Field of Search .................................. 433/91, 93, 95, 433/94, 96; 604/281, 906

[56] References Cited

U.S. PATENT DOCUMENTS

| | | | |
|---|---|---|---|
| 2,637,106 | 5/1953 | Otis | 433/91 |
| 3,086,289 | 4/1963 | Orsing | 433/96 |
| 3,885,312 | 5/1975 | Nordin | 433/96 |
| 4,017,975 | 4/1977 | Johnson | 433/91 |
| 4,325,695 | 4/1982 | Sundelin et al. | 433/91 |
| 4,906,188 | 3/1990 | Moseley | 433/93 |
| 5,078,602 | 1/1992 | Honoshofsky | 433/91 |
| 5,080,587 | 1/1992 | Miyao | 433/96 |
| 5,509,802 | 4/1996 | Whitehouse et al. | 433/96 |

FOREIGN PATENT DOCUMENTS

| | | |
|---|---|---|
| 7900546 | 8/1979 | WIPO . |
| 8200764 | 3/1982 | WIPO . |
| 9513031 | 5/1995 | WIPO . |

Primary Examiner—Ralph A. Lewis
Attorney, Agent, or Firm—Tarolli, Sundheim, Covell, Tummino & Szabo

[57] ABSTRACT

The present invention relates to a method for the production or manufacture of a suction hose (3) as well as a suction hose (3) for saliva ejection, which suction hose (3) is preformed to an arcuate hose member (14) with two shanks (15, 16) and built-in elastic properties for generating return or resetting forces (K).

14 Claims, 5 Drawing Sheets

METHOD FOR THE PRODUCTION OF A SUCTION HOSE FOR SALIVA EJECTION AND A SUCTION HOSE FOR SALIVA EJECTION

BACKGROUND OF THE INVENTION

The present invention relates to a method for the production of a suction hose for saliva ejection, which suction hose is adapted to be located in an ejecting or suction position in the mouth of a patient and to be retained in this position by bringing it to engage the chin of the patient. The invention also relates to a suction hose for saliva ejection.

Suction hoses for saliva ejection are often manufactured as a straight hose of polyvinyl chloride material (PVC-material) with one or more metallic forming wires. These wires can be bent for bending the straight hose to any suitable shape for adapting said hose to the patient. The forming wire/wires enables/enable the suction hose to maintain its bent shape.

Since said suction hoses consist of PVC- as well as metallic material, they are difficult to destruct in a non-polluting manner, particularly since the PVC-material is regarded as a biological danger.

SUMMARY OF THE INVENTION

The object of the present invention is to eliminate this problem and provide a method for the production of suction hoses which are entirely recoverable.

Since the suction hose is manufactured with a pre-bent shape, no forming wires are required and thus, the suction hose can be made of a single material which is entirely recoverable. Furthermore, the suction hose is from the beginning given an advantageous shape and elasticity.

Since the suction hose and a suction body mounted on said suction hose cling to each other, it is ensured that said suction body, after mounting on the suction hose, can not loosen completely therefrom and glide down into the throat of the patient.

BRIEF DESCRIPTION OF THE DRAWINGS

The invention will be further described below with reference to the accompanying drawings, wherein.

DETAILED DESCRIPTION OF PREFERRED EMBODIMENTS

Figure 1:
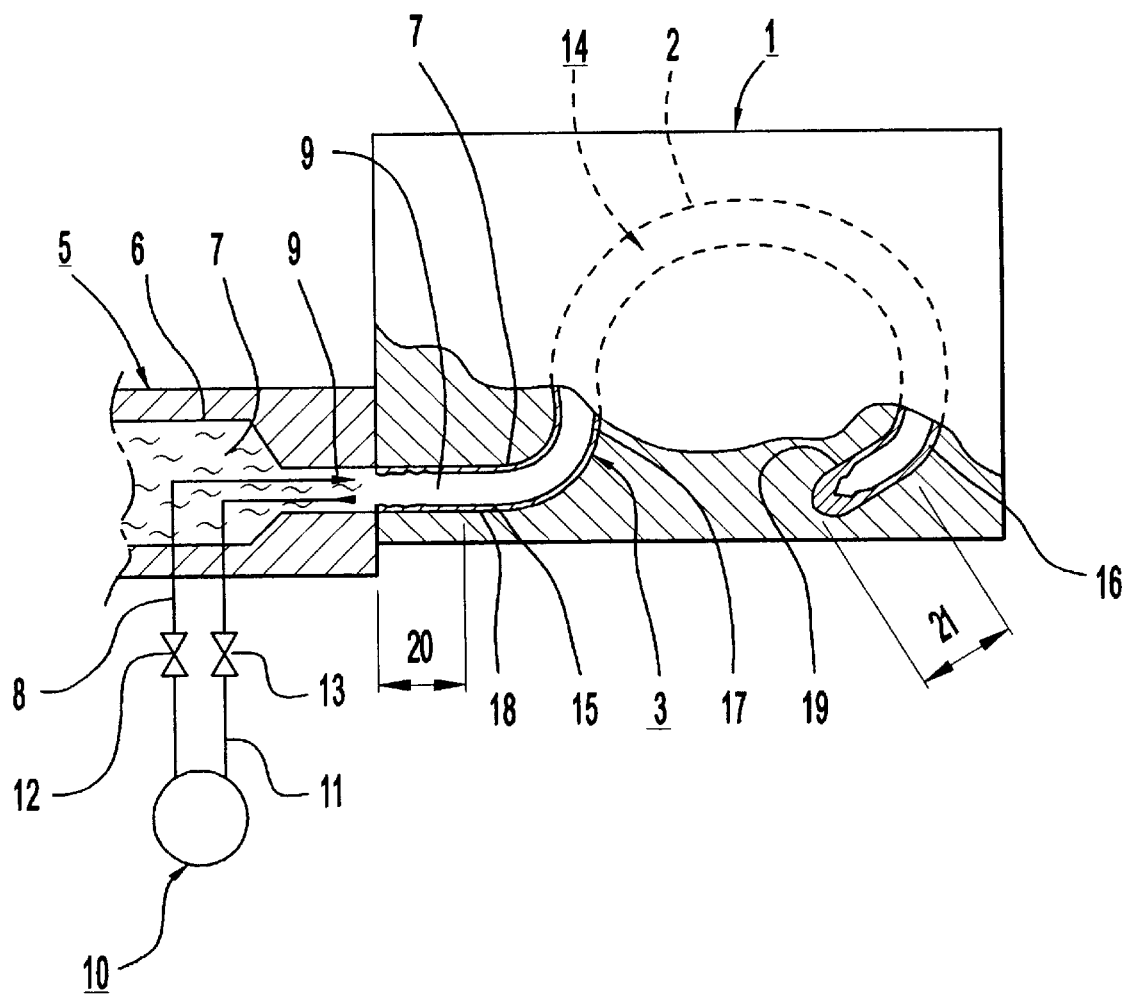
FIG. 1 is a side view taken partly in section illustrating a mold device for carrying through the method of the invention and producing a suction hose for saliva ejection.
Figure 2:
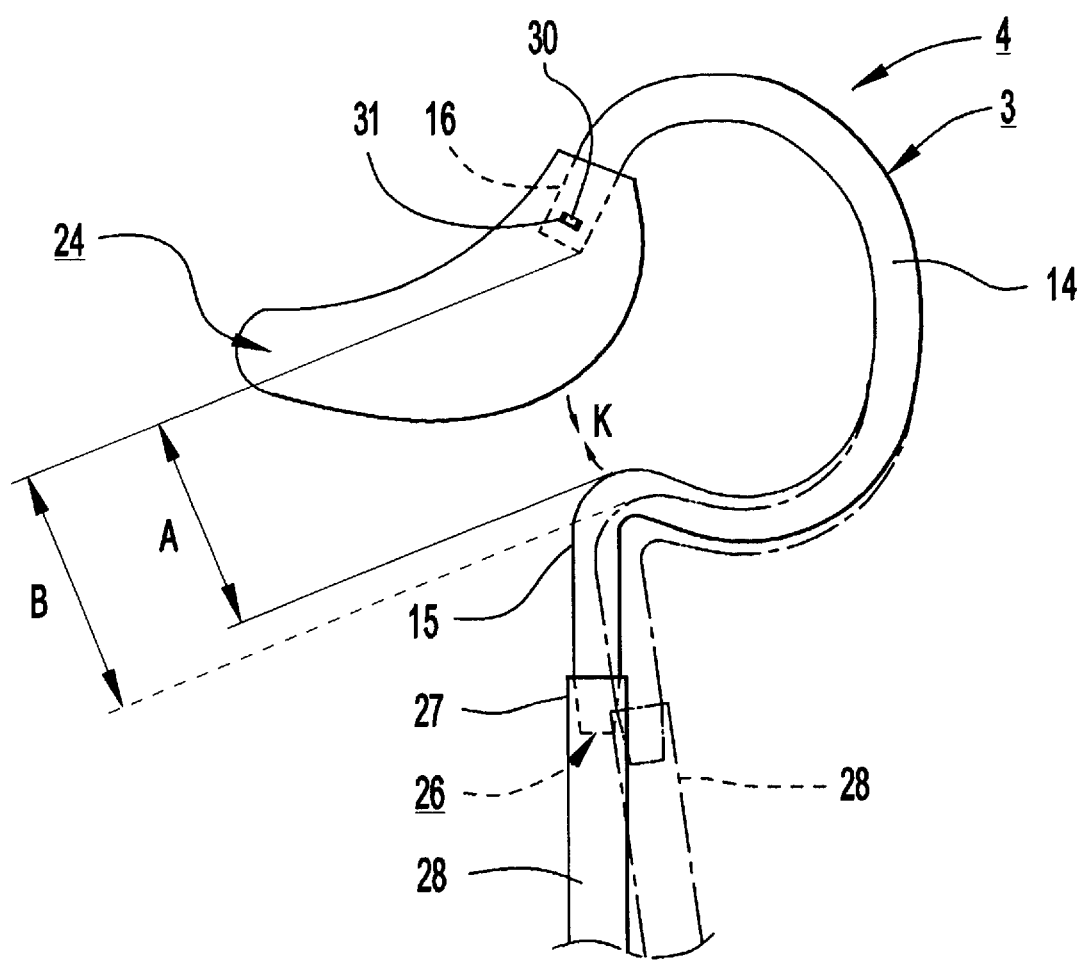
FIG. 2 is a side view illustrating a suction hose produced in the mold device of FIG. 1.
Figure 3:
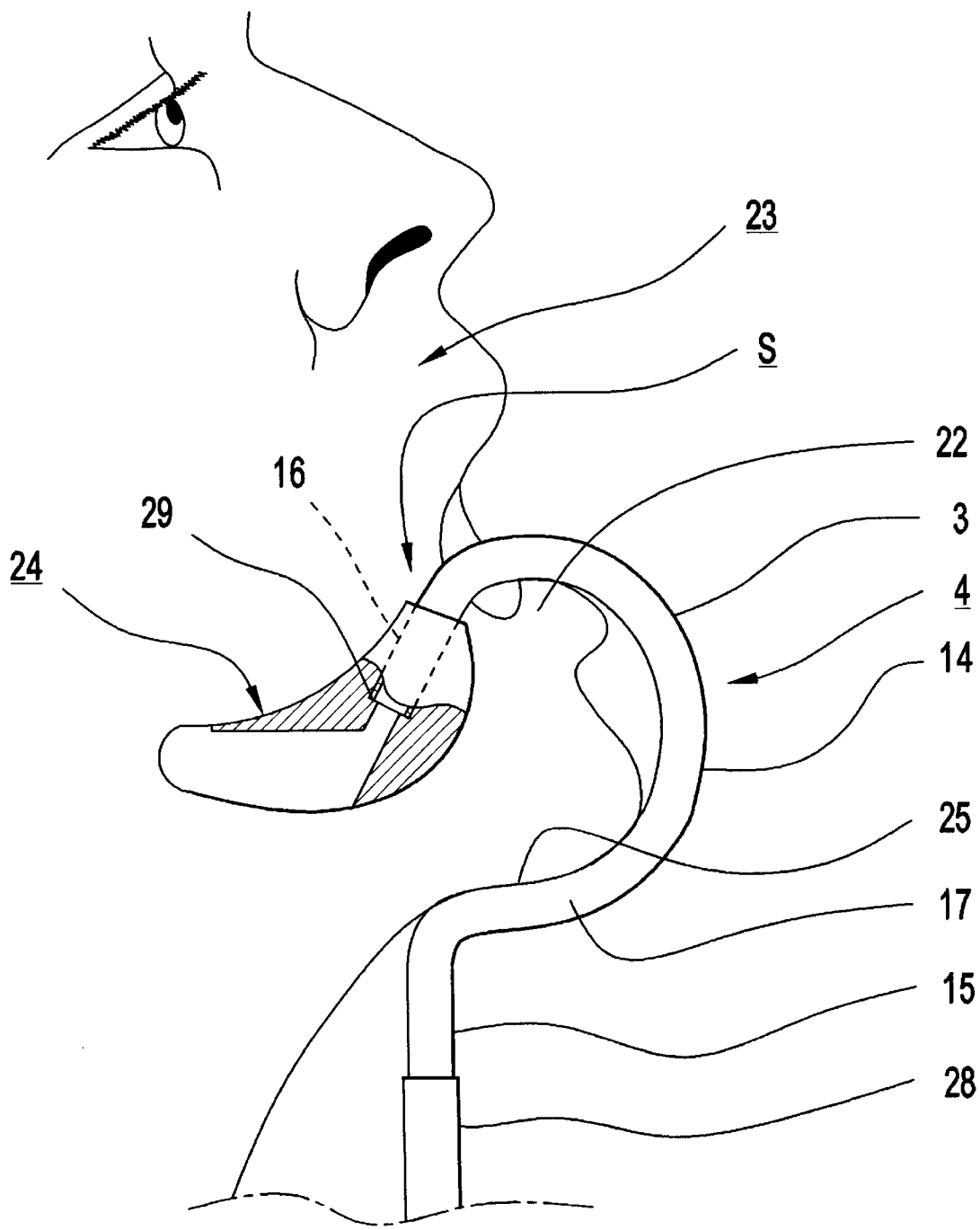
FIG. 3 is a side view illustrating a suction hose according to FIG. 2 during use on a patient.

In FIG. 1 there is illustrated a molding tool 1 with a cavity 2 for the production of a suction hose 3 for a saliva ejector 4. A nozzle 5 can be connected to the molding tool 1 so that said nozzle communicates with the cavity 2. The nozzle 5 has a passage 6 for liquid polymer material 7, preferably polyethylene material, which is pressurized towards the cavity 2. The nozzle 5 further comprises a gas conduit 8 for the supply of nitrogen gas 9 or another suitable gas at high pressure from a container 10.

The method for manufacturing the suction or ejector hose 3 is initiated by simultaneously feeding or injecting the polymer material 7 and the nitrogen gas 9 into the cavity 2 so that the nitrogen gas 9 pushes the polymer material 7 against the cavity walls, so that said material forms a thin-walled suction hose 3. This gas-assist injection molding is already known and is therefore not described in detail here. It should be mentioned, however, that there is a return conduit 11 for nitrogen gas from the cavity 2 to the gas container 10 and schematically illustrated stop valves 12, 13 are mounted in said conduits 8, 11.

The cavity 2 is designed to produce a suction hose 3 having an arcuate hose member 14 and two shanks 15, 16 protruding from opposite sides thereof. Thus, the cavity 2 is designed for producing a "preformed" arcuate hose member 14, which is bent in more than 180°, preferably 220°–260°. Furthermore, the cavity 2 is preferably designed so that the distance A between the shanks 15, 16 is 15–35 mm and that one shank 15 includes an S-shaped member 17 through which it is transformed into the arcuate hose member 14 while the other shank 16 has no such S-shaped member. The cavity 2 is also designed so that the shank 16 is substantially straight and that the shank 15 forms a straight member in connection with said S-shaped member 17. Also, two extended portions 18, 19 are located at the beginning and at the end of the cavity 2 for receiving rough and defective reject portions 20 and 21 which are often formed by this type of injection molding processes and which must be removed after removal of the suction hose 3 from the cavity 2.

During the manufacture, the shape, wall thickness and polymer material are selected so that the arcuate hose member 14 gets elastic properties which permit said member 14 to spring back when it is expanded by increasing the distance between the shanks 15, 16 (e.g. from the distance A to the distance B between said shanks 15, 16). The return or resetting force K thus obtained, is used for locating the saliva ejector 4 in a suction position S in the mouth 22 of a patient 23 so that a suction or ejector body 24 is situated in the mouth or oral cavity 22 at the root of the tongue while the S-shaped member 17 of the shank 15 engages the chin 25 of the patient 23. The elastic properties of the hose member 14 are preferably selected so that the magnitude of the return force K is limited in order to avoid providing discomfort for the patient 23 due to unpleasant pressure in the mouth 22 and/or against the chin 25.

One shank 15 of the suction hose 3 may include a conically tapering end portion 26 for enabling connection of said suction hose 3 to unequally sized coupling portions 27 on suction means 28, e.g. hoses, for sucking out saliva from the suction hose 3.

When using a particular suction or ejector body 24 it should be mentioned that said body has a passage 29 into which the shank 16 is inserted. The shank 16 may include one or another suitable number of hook portions 30 and the suction body 24 may have a recess 31 for each hook portion 30, whereby the recess 31 is larger than the hook portion 30 so that said hook portion 30 is received with clearance in said recess 31. Hereby, the suction body 24 will be somewhat pivotable relative to the shank 16 when said suction body 24 is mounted thereon.

Figure 4:
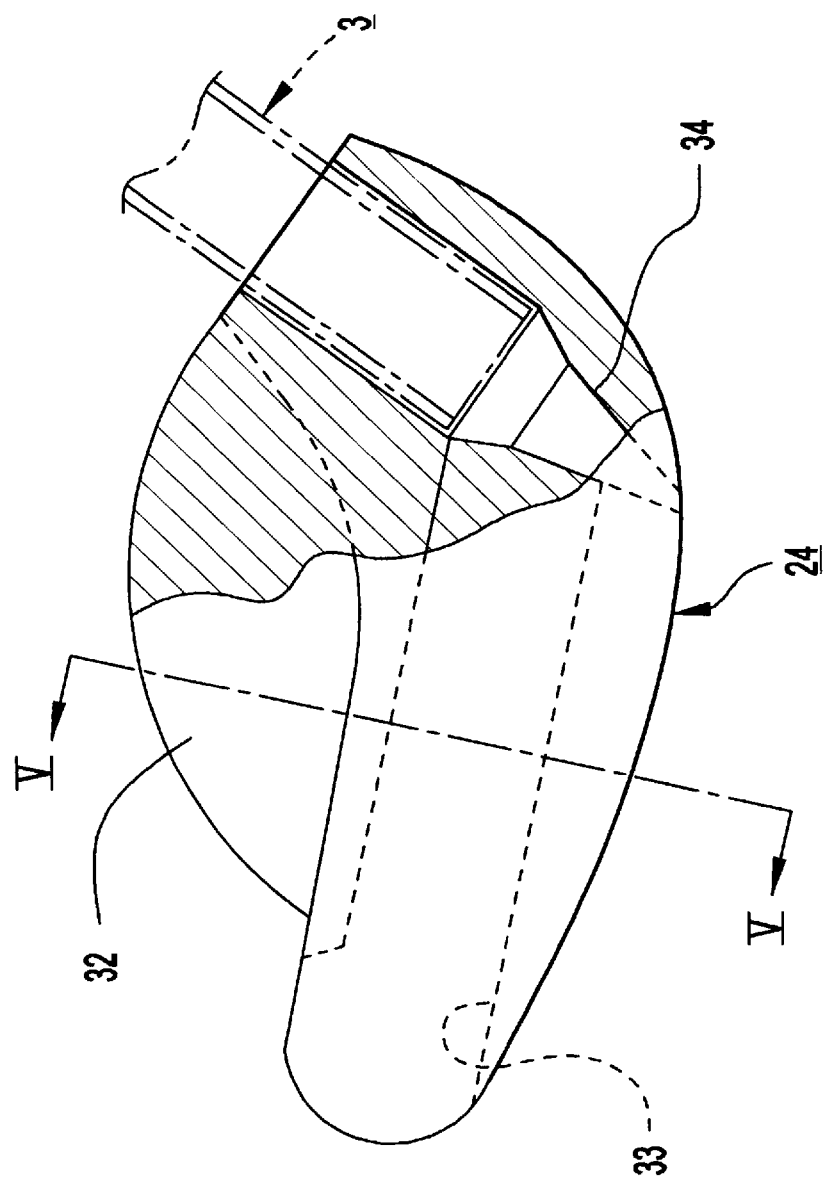
FIG. 4 is a side view illustrating a suction hose with a suction body of different shape than the one illustrated in FIG. 3.
Figure 5:
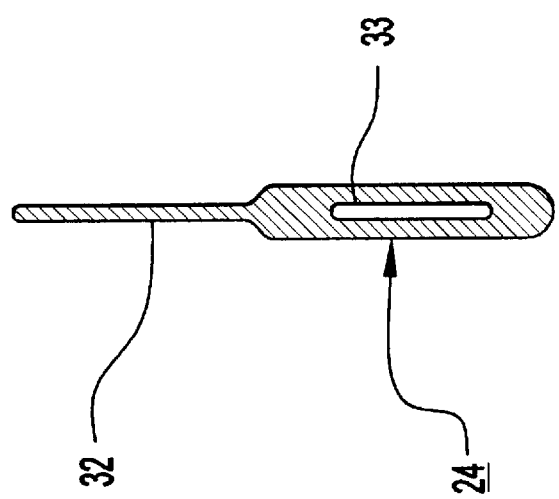
FIG. 5 is a section V—V through the suction body of FIG. 4.

The suction body 24 illustrated in FIG. 4 is at the top provided with an upwardly directed flange 32. As is shown in FIG. 5, the flange 32 is thinner than the members of the suction body 24 located beneath said flange 32. The flange 32 is adapted to define a barrier between the patient's tongue and the point of treatment and since it is thinner than other parts of the suction body 24, it does not need much space in the mouth.

The suction body 24 of FIGS. 4 and 5 is known and has a forward suction passage 33 which communicates with a rear suction passage 34. This is in turn connected to the suction hose 3 which in FIG. 4 is illustrated with dashed lines.

Figure 6:
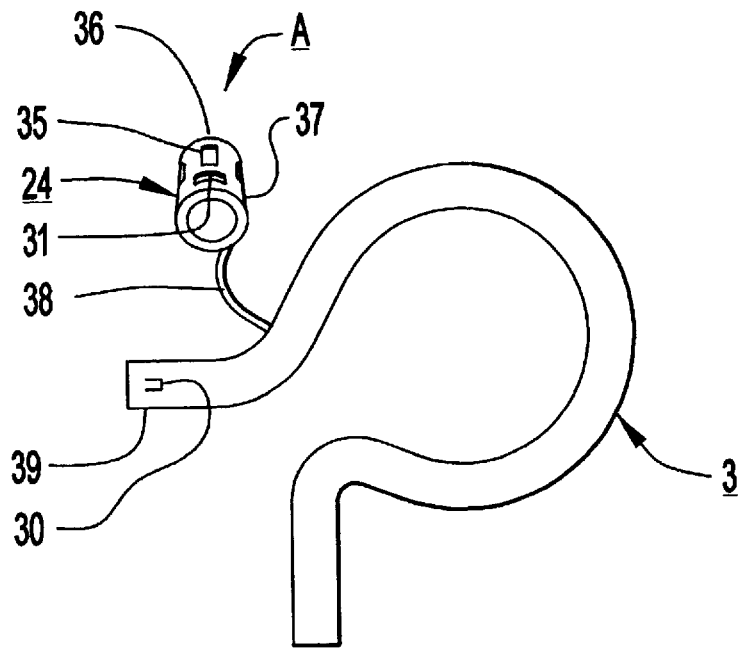
FIG. 6 is a side view illustrating a suction hose with an associated suction body of another appearance than the suction bodies in the preceding figs.
Figure 7:
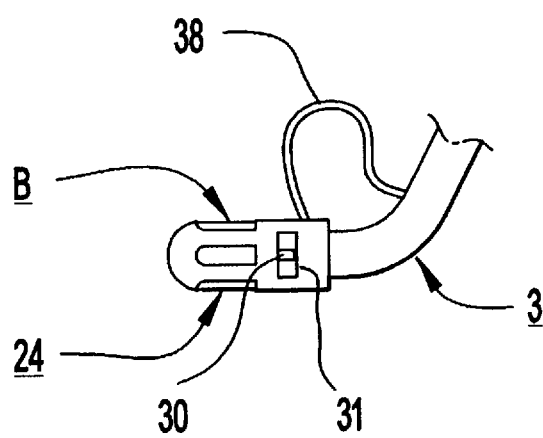
FIG. 7 illustrates the suction hose and suction body of FIG. 6 with the suction body mounted on the suction hose.

FIG. 6 illustrates a hose 3 with a suction body 24 attached thereto. This suction body consists of, in contrast to the suction bodies described above, a tube piece with lateral apertures 35, a completely or partly closed front member 36 and an open rear member 37. This suction body 24 is connected with the suction hose 3 through at least one retaining means 38 which permits relocation or displacement of the suction body 24 from an unassembled position A (see FIG. 6) for assembly or mounting in a suction position B (see FIG. 7) on a connecting member 39 of the suction hose 3.

The retaining means 38 can be a flexible band of the same or similar material as the suction hose 3 and/or the suction body 24. Furthermore, the retaining means 38 may at an outer end be provided with the suction body 24 and at an inner end be mounted on the suction hose 3 adjacent the connecting member 39, so that the suction body 24 can be mounted on the suction hose 3 in its suction position B by threading said body 24 onto said connecting member 39 until the hook portion 30 of the suction hose 3 snaps into the recess 31 in the suction body 24.

Through this latter embodiment, the suction hose 3 and the suction body 24 can be manufactured unassembled relative to each other but attached to each other. Hereby, the suction hose and associated suction body are held together during packing of the members and storing and use thereof, while it at the same time is ensured that the suction body does not loosen completely from the suction hose so that said body can glide down into the throat of the patient during dental treatment.

The method or object according to the invention described above, may vary within the scope of the following claims. It should be mentioned that it is not necessary to connect a suction body 24 to the suction hose 3, but the shank 16 of said hose can be designed so that it permits effective suction of saliva. Additionally, it should be mentioned that the suction hose 3 may be manufactured of only one material without forming wires which maintain its bent shape. Also, the suction hose 3 may consist of another thermoplastic material than polyethylene.

The suction hose 3 can be used for other purposes within the area of medical technique than for saliva ejection.

I claim:

1. An apparatus for ejecting saliva from a mouth of a person, said apparatus comprising:

a hose member comprising a one-piece tubular part made of a homogeneous material having elastic properties, said hose member having a continuous outer surface and a continuous inner surface defining a fluid passage through said hose member for ejecting saliva, said hose member including a middle portion extending between first and second shank portions located adjacent respective terminal ends of said hose member, said first and second shank portions being elastically movable away from one another against a return force tending to oppose movement of said shank portions away from one another, said middle portion of said hose member having a C-shape defined by an upper section, a lower section and a central section extending between said upper and lower sections, said upper section adjoining said first shank portion of said hose member and said lower section adjoining said second shank portion of said hose member, said upper section for extending into and engaging the mouth of the person and said lower section for directly clampingly engaging a chin of the person to hold said hose member in a suction position on the person using said return force.

2. The apparatus of claim 1 wherein said middle portion of said hose member is arcuate and extends circumferentially in an arc ranging from 220° to 260°.

3. The apparatus of claim 1 wherein said first and second shank portions of said hose member are separated by a distance of 15 mm to 35 mm.

4. The apparatus of claim 1 wherein said first shank portion of said hose member includes a hook portion for attaching a suction body to said hose member.

5. The apparatus of claim 1 further comprising a suction body for placement inside the mouth of the person, said suction body being connected with said hose member and having at least one suction passage in fluid communication with said fluid passage in said hose member.

6. The apparatus of claim 5 wherein said first shank portion of said hose member includes a hook portion and said suction body includes a recess for receiving said hook portion to attach said suction body to said hose member.

7. The apparatus of claim 6 wherein said hook portion is received in said recess with sufficient clearance to allow said suction body to pivot relative to said first shank portion of said hose member.

8. The apparatus of claim 6 wherein said suction body is detachably connected with said hose member by at least one flexible band extending between said first shank portion and said suction body, said at least one flexible band permitting said suction body to be disassembled from said hose member but remain connected with said hose member.

9. The apparatus of claim 6 wherein said suction body includes an upwardly directed flange having a thinner cross-section than other portions of said suction body.

10. The apparatus of claim 1 wherein said second shank portion of said hose member includes a conically tapering portion for connecting suction means for sucking saliva through said hose member.

11. The apparatus of claim 1 wherein said hose member is made of a polymeric material which provides said hose member with said elastic properties and with rigidity sufficient to maintain the arcuate shape of said middle portion.

12. The apparatus of claim 1 wherein said hose member is made of polyethylene.

13. The apparatus of claim 1 wherein said hose member is manufactured using a gas-assisted injection molding process.

14. The apparatus of claim 1 wherein said hose member is movable between a free position and said suction position, said first and second shank portions being farther apart when said hose member is in said suction position than when said hose member is in said free position, said return force tending to return said hose member to said free position when said hose member is in said suction position.

* * * * *